US005652115A

United States Patent [19]
Marks et al.

[11] Patent Number: 5,652,115
[45] Date of Patent: Jul. 29, 1997

[54] METHOD OF DETECTING TUMORS CONTAINING COMPLEXES OF P53 AND HSP70

[75] Inventors: Jeffrey Robert Marks, Hillsborough; James Dirk Inglehart; Andrew Mark Davidoff, both of Durham, all of N.C.; Jerry G. Henslee, Libertyville, Ill.

[73] Assignee: Duke University, Duram, N.C.

[21] Appl. No.: 276,872

[22] Filed: Jul. 18, 1994

Related U.S. Application Data

[63] Continuation of Ser. No. 968,818, Oct. 30, 1992, abandoned, which is a continuation-in-part of Ser. No. 869,292, Apr. 14, 1992, abandoned.

[51] Int. Cl.$^6$ .................... G01N 33/574; G01N 33/53
[52] U.S. Cl. .................... 435/7.23; 435/7.93; 435/7.95; 435/7.94; 436/506; 436/503; 436/64; 436/813
[58] Field of Search ................... 435/7.23, 7.93, 435/7.95, 7.94; 436/506, 503, 64, 813; 530/389.7

[56] References Cited

U.S. PATENT DOCUMENTS 4,937,185  6/1990  Webb et al. .................... 435/7.23

FOREIGN PATENT DOCUMENTS

| 0 204 922 | 3/1986 | European Pat. Off. |
| 0 390 323 | 5/1990 | European Pat. Off. |
| WO 90/07117 | 6/1990 | WIPO . |
| WO 91/06572 | 5/1991 | WIPO . |

OTHER PUBLICATIONS

Lehman et al., *Cancer Res.* 51, 4090–4096 (1991).
Urban et al., *Ann. Rev. Immunol.* 10, 617–644 (1992).
Cossman et al., *J. Natl. Cancer Inst.* 83, 980–981 (1991) (Editorial).
Bellanti *Immunology.* W. B. Saunders Co., Philadelphia, pp. 49–54 (1971).
Trivers et al., in "Proceedings of the Eighty–Third Annual Meeting of the American Association for Cancer Research," May 20–23, 1992, San Diego, California, vol. 33, Mar. 1992 (Abstract No. 1745).
Winter et al., *Cancer Research* 52, 4168–4174 (1992).
J. Barque et al., *The EMBO Journal* 2, 743–749 (1983).
C. Caron de Fromentel et al., *Int. J. Cancer* 39, 185–189 (1987).
L. Crawford et al., *Mol. Biol. Med.* 2, 261–272 (1984).
L. Crawford et al., *Int. J. Cancer* 30, 403–408 (1982).
A. Davidoff et al., *Proc. Natl. Acad. Sci. USA* 88, 5006–5010 (1991).
O. Halevy et al., *Science* 250, 113–116 (1990).
P. Hinds et al., *Cell Growth & Differentiation* 1, 571–580 (1990).
Tijssen, 1985. *Practice and Theory of Enzyme Immunoassays*, Elsevier, Amsterdam. pp. 481–483.
Davidoff et al, 1992 (Apr.). Immune Response to p. 53 is Dependent Upon P53/HSP70 Complexes in Breast Cancers. Proc. Natl. Acad Sci 89:3439–3442.

*Primary Examiner*—Toni R. Scheiner
*Attorney, Agent, or Firm*—Cheryl L. Becker

[57] ABSTRACT

The present invention relates to the finding that the class of mutant p53 proteins which bind to HSP70 defines a group of mutant p53 proteins which elicit serum autoantibodies. Thus, disclosed is a method of classifying tumor cells for the ability to produce serum p53 autoantibodies in a patient carrying such tumor cells, a method of detecting tumor cells containing a mutant p53 protein capable of forming a complex with a 70 kilodalton heat shock protein (hsp70) in the cells in a patient, a method of distinguishing tumor cells capable of causing more aggressive disease in a patient carrying the tumor cells, and a method of monitoring a patient for the recurrence of disease in a patient previously diagnosed as carrying tumor cells.

5 Claims, 5 Drawing Sheets

METHOD OF DETECTING TUMORS CONTAINING COMPLEXES OF P53 AND HSP70

RELATED APPLICATIONS

This is a continuation of pending application Ser. No. 07/968,818 filed 30 Oct. 1992, now abandoned which is a continuation-in-part of application Ser. No. 07/869,292, filed 14 Apr. 1992, now abandoned the disclosure of which is to be incorporated herein by reference.

This invention was made with Government support under NCI Grant 1 F32 CA08899-01. The Government has certain rights to this invention.

FIELD OF THE INVENTION

The present invention relates to the finding that the class of mutant p53 proteins which bind to HSP70 defines a group of mutant p53 proteins which elicit serum autoantibodies.

BACKGROUND OF THE INVENTION

Mutations in the p53 tumor suppressor gene are found at a high frequency in a wide variety of primary human cancers. See, e.g., M. Hollstein et al., *Science* 253, 49–53 (1991). Breast cancer is typical of human carcinomas with respect to p53 involvement, and it has been reported that approximately 10% of breast cancer patients have circulating antibodies directed against the p53 protein. L. Crawford et al., *Int. J. Cancer* 30, 403–408 (1982). The diagnostic significance of circulating p53 antibodies has, however, been uncertain: it has subsequently been found that 21% of patients with benign mammary fibroadenomas show elevated levels of the p53 protein in tumor tissue samples, and that more than half of patients with serum p53 antibodies show no elevation of the p53 protein in tumor tissue. L. Crawford et al., *Mol. Biol. Med.* 2, 261–272 (1984).

SUMMARY OF THE INVENTION

In the study leading to the present invention, p53 immunogenicity was examined in breast cancer patients with particular regard to the type of p53 mutant being expressed by tumor cells and the ability of these proteins to bind the 70 kd heat shock protein. As discussed in detail below, we have now found that the class of mutant p53 proteins which bind to HSP70 defines a group of mutant p53 proteins which elicit serum autoantibodies. Because p53 proteins which bind HSP70 tend to be more tumorigenic, see P. Hinds et al., *Cell Growth Differ.* 1, 571–580 (1990); O. Halevy et al., *Science* 250, 113–116 (1990), this finding provides a way to use serum p53 auto antibodies for the diagnosis and prognosis of disease.

In view of the foregoing, a first aspect of the present invention is a method of classifying tumor cells for the ability to produce serum p53 autoantibodies in a patient carrying such tumor cells. The method comprises collecting a sample of tumor cells from the patient, and then detecting (e.g., by coimmunoprecipitation) the presence of a complex of the p53 protein and a 70 kilodalton heat shock protein (hsp70) in the tumor cells. The presence of this complex indicates that the tumor cells are capable of eliciting serum p53 autoantibodies in the patient. In one embodiment, the tumor cells are contained within a tumor (e.g., a primary tumor), and the detecting step is carried out concurrently with the step of removing the tumor from the patient; in another embodiment, the tumor cells are contained within a tumor (e.g., a primary tumor), and the detecting step is followed by the step of removing the tumor from the patient. The step of removing the tumor from the patient may optionally be followed by the step of detecting the appearance of serum p53 autoantibodies in the patient, the appearance of said autoantibodies indicating the growth or presence of the tumor cells in the patient.

A second aspect of the present invention is a method of detecting tumor cells expressing a mutant p53 protein capable of forming a complex with a 70 kilodalton heat shock protein (hsp70). The method comprises collecting a sample of biological fluid from the patient, and then detecting p53 autoantibodies in the biological fluid, the presence of p53 autoantibodies in the biological fluid indicating the tumor cells express a mutant p53 protein capable of forming a complex with hsp70.

A third aspect of the present invention is a method of distinguishing tumor cells capable of causing a more aggressive disease in a patient carrying the tumor cells. The method comprises collecting a sample of a biological fluid from the patient, and then detecting p53 autoantibodies in the biological fluid, the presence of p53 autoantibodies in the biological fluid indicating the tumor cells are capable of causing a more aggressive disease.

A fourth aspect of the present invention is a method of monitoring a patient for the recurrence of disease in a patient previously diagnosed as carrying tumor cells, and which patient has previously undergone treatment to reduce the number of said tumor cells. The method comprises collecting a sample of biological fluid from the patient, and then detecting p53 autoantibodies in the biological fluid, the presence of p53 autoantibodies in the biological fluid indicating that the number of the tumor cells in the patient has increased. Typically, the treatment referred to is one effective to reduce the amount of p53 autoantibodies in the biological fluid, and the tumor cells express a mutant p53 protein capable of forming a complex with a 70 kilodalton heat shock protein in said cells. The detecting step may be repeated on a plurality of occasions to provide continued monitoring for the recurrence of disease. The method may optionally further comprise the step of detecting p53 autoantibodies in the patient prior to the treatment.

A fifth aspect of the present invention is a prognostic method for detecting aggressive disease in a patient not previously diagnosed as carrying tumor cells. The method comprises collecting a sample of biological fluid from the patient, and then detecting p53 autoantibodies in the biological fluid. The presence of p53 autoantibodies in the biological fluid indicates that the patient harbors tumor cells which are more aggressive.

A sixth aspect of the present invention is a diagnostic method for detecting cancer in a patient. The method comprises collecting a sample of biological fluid from the patient, and then detecting p53 autoantibodies in the biological fluid. The presence of p53 autoantibodies in the biological fluid indicates that the patient harbors tumor cells.

The foregoing and other objects and aspects of the present invention are explained in detail in the drawings herein and the specification set forth below.

DETAILED DESCRIPTION OF THE INVENTION

Figure 1:
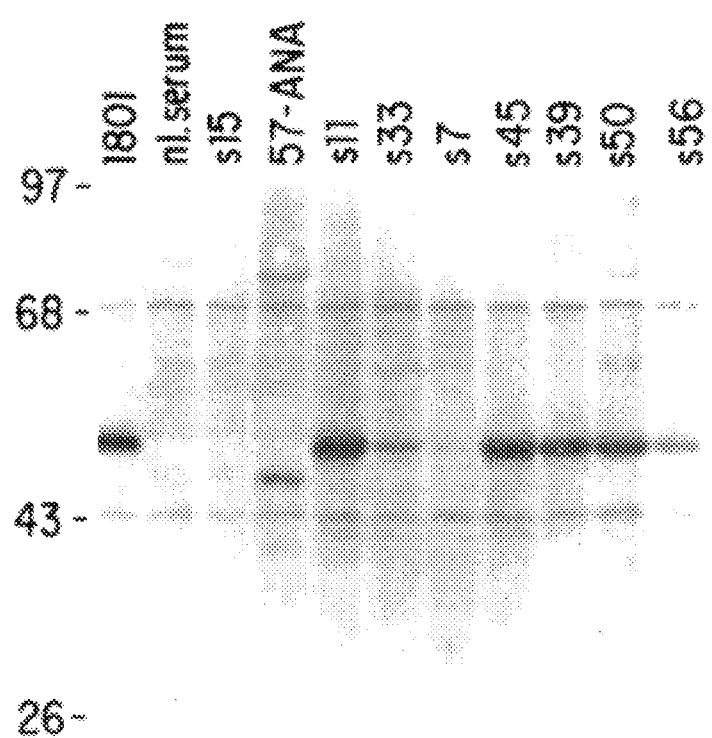
FIG. 1 shows the screening of sera from patients with breast cancer for anti-p53 antibodies. Immunoprecipitation of metabolically labeled protein extracts from the breast cancer cell line, BT-20, with: PAb1801; normal human serum (nl); s15 is from a breast cancer patient whose tumor did not overexpress p53 protein; 57-ANA is from a patient with other (undefined) anti-nuclear antibodies; s11, s33, s7, s45, s39, s50, and s56 are from breast cancer patients whose tumors expressed high levels of mutant p53 protein.

The method disclosed herein may be employed with patients suspected of carrying cancer (including, but not limited to, cancers of both endothelial and epithelial origin such as colo-rectal, lung, breast, or ovarian cancer tumor cells), particularly breast cancer, and may be employed both to monitor patients who have been previously diagnosed as carrying cancer (including patients who have undergone treatment for the cancer) and to screen patients who have not been previously diagnosed as carrying cancer. Patients are typically human males and females, though veterinary applications for the present invention (i.e., in the treatment of dogs, cats, horses, etc.) are also contemplated. Where previous diagnosis is carried out, the diagnosis is typically through the identification of a mass upon palpation, radiological diagnosis, cytology, or the detection of a humoral marker. Treatment of the cancer is typically through cytoreductive surgery, through administration of antineoplastic agents, or combinations thereof such as cytoreductive surgery followed by treatment with antineoplastic agents.

As noted above, the present invention can be used for diagnosing whether a patient has cancer, and wheter it is a more aggressive form of cancer. The present invention also provides a method for subsequent monitoring of a patient for tumor recurrence. In patients bearing cancers that express mutant p53 proteins, an antibody response to the p53 protein is sometimes induced. Upon removal of the tumor, the antibody response regresses. In cases where the patient forms a tumor at a secondary site, i.e., a metastasis, the antibody response reappears. This antibody response is specific for patients bearing tumors that contain p53 mutations. Therefore, by assaying for the presence of the p53 antibodies, the presence or absence of the tumor can be determined. However, only a subset of p53 mutant proteins induce this immune response. This subset has now been identified as those p53 mutant proteins that can form stable complexes with hsp70. The presence of this complex can be assayed in primary tumor tissue by means such as coimmunoprecipitation with antibodies to p53 and hsp70. Therefore, with a sample of the primary tumor tissue, it can be predicted which patients will mount an antibody response to p53. This is useful if the primary tumor is too small to efficiently induce the response or the patient has been pretreated with chemotherapy or radiation which has obliterated or obscured the immune response. When the patient has recovered their immune response and upon tumor recurrence, they would be expected to mount an immune response which can be readily assayed. Also, an immune response which can be assayed would occur when the primary tumor has grown to a size sufficient to cause an immune response, such is also the case where secondary or metastasized tumors cause an immune response, as in the case of a relapse. If the p53/hsp70 complex is detected in the primary tumor, the patient would be monitored for the appearance of a p53 antibody response which would signal tumor recurrence.

The phrase "more aggressive disease" as used herein refers to (a) disease which arises from cancer cells which grow rapidly; (b) disease which arises from cancer cells which undergo rapid metastasis; and (c) disease for which there is a high probability of recurrence after treatment.

Samples taken from patients for use in the detecting steps described herein are generally biological fluids such as serum, blood plasma, or ascites fluid. Serum and blood plasma, particularly serum, is preferred. The patient need not be one currently harboring tumor cells, as autoantibodies may be expected to remain in a patient for some time after all cells which generated such antibodies have been removed before eventually dissipating.

Where samples are taken from a patient for the purpose of detecting the recurrence of disease, the samples are preferably taken at a time after the treatment (surgical, chemical, etc.) sufficient in duration for residual autoantibodies to have dissipated. In general, the collecting step is carried out at least six weeks after the treatment, but may be carried out three months, six months, or even one year after the treatment (where the treatment involves a course of treatments, such as a course of chemotherapy, this time is measured from the last occurence thereof). Such samples may be collected from the patient periodically, on several occasions, to provide continued monitoring for the recurrence of disease. The time period between taking such samples will vary depending on the type and status of disease: typically, samples are collected at intervals of from six months to one year, but when the patient has undergone treatment for advanced cancer, the interval between collection may be about 3 months. Subsequent treatment regimes may, if desired, be initiated while the monitoring program initiated with the previous treatment is still being carried out.

The step of detecting p53 autoantibodies in the sample of biological fluid may be carried out in accordance with known techniques. See, e.g., L. Crawford et al., *Int. J. Cancer* 30, 403–408 (1982); L. Crawford et al., *Mol. Biol. Med.* 2, 261–272 (1984). Examples of suitable assays include radioimmunoassay, immunofluorescence assays, enzyme-linked immunoassays, and the like. Those skilled in the art will be familiar with numerous specific immunoassay formats and variations thereof which may be useful for carrying out the method disclosed herein. See generally E. Maggio, *Enzyme-Immunoassay,* (1980) (CRC Press, Inc., Boca Raton, Fla.).

The present invention is explained in greater detail in the following examples. The examples show, among other things, that (1) mutant p53 proteins which bind HSP70 elicit serum autoantibodies; (2) conversely, the presence of anti-p53 autoantibodies reflects the presence of a p53 mutation which binds hsp70; (3) the presence of an anti-p53 autoantibody therefore establishes the presence of a growth within the body of a subject which produces an hsp70-binding mutant p53; (4) detection of an anti-p53 autoantibody can be used to determine the class of p53 mutant produced within the body; (5) detection of an anti-p53 autoantibody will determine that a growth somewhere in the body is cancerous and is producing an hsp70-binding p53 mutant protein; and (6) detection of p53 autoantibody indicates a more aggressive tumor. In example 1, Jack Keene, Eric Winer and Robert Bast of Duke University, Durham, N.C., supplied patient sera. Temperatures are given in degrees Centigrade unless otherwise indicated.

EXAMPLE 1

I. Material and Methods

Tissue.

Pieces from breast biopsies and mastectomies performed at Duke University Medical Center were collected after surgical removal, immediately flash frozen, and stored at −120° C. Specimens from sixty patients whose tumors were diagnosed as primary invasive breast carcinoma by a member of the Department of Pathology were studied. Thirty of these tumors had been shown, by immunohistochemical analysis, to overexpress the p53 protein, while thirty expressed normal, low levels of the protein.

Cell lines.

The established cell lines HBL100, BT-20, BT-474, T47D and MDA-MB-468 were obtained from the American Type Culture Collection. HBL100 is an SV40-transformed human breast epithelial cell line which expresses wild-type p53 (24); BT20, BT474, T47D and MDA-MB-468 are human breast cancer-derived cell lines that express p53 proteins with mutations at codons 132, 285, 194, and 273 respectively. See J. Nigro et al., *Nature* 342, 705–708 (1989); J. Bartek et al., *Oncogene* 5, 893–899 (1990). The I3 cell line, obtained from Dr. Cathy A. Finlay (Department of Molecular Biology, Princeton University), is a rat embryo fibroblast line immortalized by the murine mutant p53 clone LTRcG-val$^{135}$. P. Hinds et al., *J. Virol.* 63, 739–746 (1989). Cells were grown at 37° C. in RPMI 1640 supplemented with bovine insulin (10 μm/ml), glutamine (300 mg/L), and 10% fetal calf serum. Normal human mammary epithelial cells (HMEC) were collected following reduction mammoplasties and maintained in short term culture in accordance with standard techniques. See V. Band & R. Sager, *Proc. Natl. Acad. Sci. USA* 86, 1249–1253 (1989).

Antibodies.

Serum from patients with primary, invasive breast cancer was obtained at the time of diagnosis and stored at −20° C. PAb1801 (Ab-2, Oncogene Science) is a murine anti-p53 monoclonal antibody which reacts specifically with human p53 at an epitope between amino acids 32 and 79. L. Banks et al., *Eur. J. Biochem.* 159, 529–534 (1986). PAb421 is a murine anti-p53 monoclonal antibody which reacts with an epitope of mammalian p53 between amino acids 370 and 378, A. Wade-Evans & J. Jenkins, *EMBO J.* 4, 699–706 (1985), and is produced by a hybridoma cell line obtained from Dr. Arnold J. Levine (Department of Molecular Biology, Princeton University). HSP72/73 (Ab-1, Oncogene Science) is a murine monoclonal antibody which reacts with HSP70 proteins in mammalian cells (clone W27, E. Harlow). Rabbit antiserum directed against human C-terminal epitopes representing the last 21 amino acids of at least the hsc70 and hsp70 members of the heat shock protein family, Philip Hinds et al., *Mol. Cell Biol.* 7, 2863–2869 (1987), was obtained from Dr. P. Hinds (Department of Molecular Biology, Whitehead Institute). TA-1, an anti-HER2/neu murine IgG$_1$ monoclonal antibody (DuPont), normal human serum, and serum from fifteen patients with anti-nuclear antibodies associated with autoimmune disorders (obtained from Dr. J. D. Keene, Department of Microbiology, Duke University) were used as control antibodies.

Sequence analysis.

Sequencing of the highly conserved region of the p53 gene from mRNA was performed in accordance with known techniques. See, e.g., A. Davidoff et al., *Proc. Natl. Acad. Sci. USA* 88, 5006–5010 (1991). Briefly, 1 μg of total RNA was used as a template for p53 first strand cDNA synthesis by MuLV reverse transcriptase (Bethesda Research Lab) using an anti-sense oligonucleotide from exon 10 as a primer. Exons 4 through 10 were then amplified using the polymerase chain reaction by adding an oligo primer from exon 4 and Taq DNA polymerase (Promega). The 712 bp product of this reaction was gel purified, reamplified, and purified again by filtration through a Sepharose CL-6B (Pharmacia) spin column, ethanol precipitated, and resolubilized in water. This material was the template for dideoxy-sequencing using Sequenase 2.0 (United States Biochemical). Oligonucleotides flanking each of the exons 5, 6, 7 and 8 were used to prime the reactions which were performed by first boiling the primer-template mix, labeling on ice for 10 min with $^{32}$P-dATP and then running the termination reactions at 45° C. for 10 min. The products were electrophoresed on a polyacrylamide gel which was then soaked in 10% acetic acid/12% methanol, dried and set with Kodak XAR film.

Immunoprecipitation.

Cell lines were metabolically labelled with 50 μCi/ml $^{35}$S-methionine (Amersham) for 2 h. At the end of the labelling period, cells were scraped, homogenized in lysis buffer (50 mM Tris, 5 mM EDTA, 150 mM NaCl, 0.5% NP40, 1 mM PMSF) and then sonicated for 10 sec at 5 W/S. The supernatants were collected following centrifugation at 100,000g and preadsorbed with protein G-Sepharose (Pharmacia) for 1 hour at 4° C. Supernatants were collected following centrifugation at 12,000g and incorporation was quantitated by trichloroacetic acid (TCA) precipitation. Immunoprecipitation of p53 was performed from 5×10$^6$ TCA precipitable counts from each cell line. The lysates were incubated at 4° C. for 1 h with 1 μl of human serum or 0.1 μg of a monoclonal antibody and the immune complexes were then bound with 20 μl protein G-Sepharose (4° C., 2 h). The Sepharose was washed three times with lysis buffer and the samples were denatured by boiling for 5 minutes in an equal volume of SDS-loading buffer (100 mM Tris pH=6.8, 4% SDS, 0.2% bromophenol blue, 20% glycerol, 50 mM β-ME) and loaded onto a 10% SDS-polyacrylamide gel. Following electrophoresis of the samples, the protein was transferred to a nitrocellulose membrane (Schleicher and Schuell) by electroblotting at 400 mA for 2 h. The membrane was dried and set with Kodak XAR film overnight.

Immunoblotting.

Protein extraction from unlabeled cell pellets and frozen tissues was performed as described above except that tissues were homogenized using a Polytron (Brinkman). 250 μg of unlabeled total protein (2 mg for HMEC and NIH3T3 cells) was reacted with patient sera or monoclonal antibodies, the recovered protein electrophoresed on an SDS-polyacrylamide gel and then transferred to a nitrocellulose membrane also as described above. The membrane was then treated in a blocking solution (3% bovine serum albumin (BSA), 0.2% Tween 20, 0.02% sodium azide and 1 mM sodium iodide in phosphate-buffered saline [PBS]) overnight and probed for 90 min at 37° C. with PAb421 supernatant diluted 1:3 in 5% BSA. After washing with PBS, the blot was probed with biotinylated F(ab')$_2$ goat anti-mouse sera (Tago) in 5 ml 5% BSA for 1 h. Following a final wash in PBS, antibody binding was visualized with an avidin conjugated immunoperoxidase detection system (Vector).

Coimmunoprecipitation.

Coimmunoprecipitation of p53 and HSP70 in tumors from patients with primary invasive breast cancer was performed by first reacting protein extracts (250 μg) from tumor tissues with either an anti-p53 antibody or anti-HSP70 antibody. Four immunoprecipitation reactions, two with each antibody, were performed on protein extracts from each tissue. For detecting HSP70 in the complex, immunoprecipitation was performed with 0.1 μg of the murine monoclonal antibodies, PAb1801 and HSP72/73. For detecting complexed p53, immunoprecipitation was performed with one of the human anti-p53 antisera, s11, and the rabbit anti-HSP70 antiserum. These immunoprecipitates were electrophoresed and blotted as described above. Probing for HSP70 was performed with 10 μl rabbit anti-HSP70 sera in 5% BSA. Probing for p53 was performed with 1.0 μg PAb1801. Heterologous species antisera were used for these immunoprecipitations since the mouse monoclonals themselves are detected as ≈50 kd proteins with the biotinylated goat anti-mouse IgG detection system. Binding was detected with biotinylated goat anti-rabbit (Vector) or anti-mouse as appropriate; visualization was again performed with an immunoperoxidase detection system.

II. Results

Detection of anti-p53 antibodies.

Sera collected in the perioperative period from 30 patients whose breast cancer expressed high levels of p53 and 30 patients whose tumor expressed undetectable p53 protein were screened for the presence of anti-p53 antibodies. 1 μl of each serum was reacted with metabolically labeled protein lysate from the established human breast cancer cell line BT20. This cell line expresses high levels of a p53 protein harboring a mutation at codon 132. See J. Bartek et al., Oncogene 5, 893–899 (1990). Sera from seven patients with tumors that overexpressed p53 contained antibodies that immunoprecipitated a 53 kd protein which co-migrated with p53 immunoprecipitated with the monoclonal antibody, PAb1801 (FIG. 1). Dilutional analysis of these sera showed >10-fold variation in their reactivity, with the strongest ones comparable to the immunoglobulin affinity-purified pAB1801. No band corresponding to a protein of this molecular weight was immunoprecipitated by any of the sera from patients with p53-negative tumors. In addition no 53 kd protein was recovered from the BT20 lysate with sera from 15 patients with autoimmune disorders who were known to have anti-nuclear antibodies.

Figure 2:
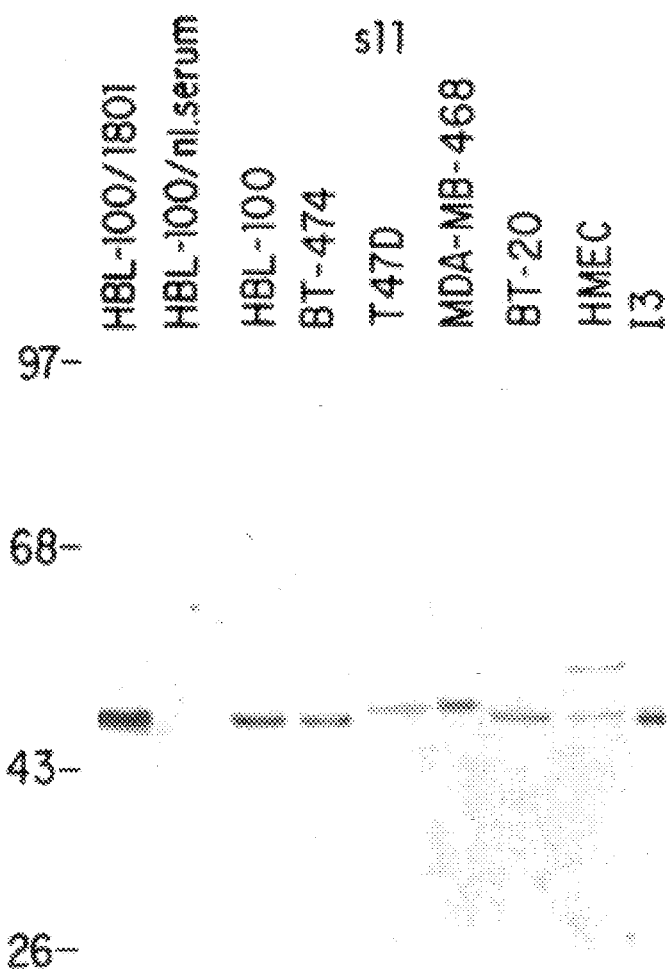
FIG. 2 shows the recovery of wild-type and a variety of mutant p53 proteins with sera from breast cancer patient s11. All seven antibody-positive sera recognized this panel of diverse p53 proteins, in addition to wild-type murine p53 from NIH3T3 cells (data not shown).

Immunoblotting was performed in order to confirm that each of these seven sera recognized the p53 oncogene. Unlabeled protein extracts were immunoprecipitated with each sera, electrophoresed, transferred to a solid support, and then probed with PAb421. The specific recovery of a 53 kd protein detected by the p53 monoclonal antibody in each case confirmed the identity of the immunoprecipitated protein (FIG. 2). Immunoprecipitation from different established human and murine cell lines revealed that each of the antisera recognized a wide range of p53 proteins, both mutant and wild-type (FIG. 2).

p53 mutations correlate with immune response.

Several possibilities could explain why only a subset of breast cancers expressing mutant p53 proteins elicit p53 antibodies. The amount of mutant protein may be highly variable and, after cell death, attain immunogenicity only in those tumors with high levels. However, by immunohistochemistry no major differences in the levels of p53 expression were observed in these tumors (data not shown). Alternatively, only certain mutant p53 proteins may be immunogenic even though the antibodies themselves are not mutant specific. To test this, direct sequencing of PCR amplified p53 cDNA was performed from 15 breast cancers overexpressing the protein. In each case, a mutation was found in a highly conserved region of the gene which altered the coding sequence of the protein (Table 1). A generally consistent clustering of these mutations was observed: Each patients who had not mounted an antibody response to p53 had a tumor that contained a mutation in exons 7 or 8 of the p53 gene. Conversely, five of seven patients who were antibody-positive had tumors with mutations in exons 5 or 6. The two exceptions were patients 33 and 45. Their tumors contained mutations at codons 275 (exon 8) and 238 (exon 7) yet the patients mounted strong immune responses. In both cases, the mutations changed a cysteine residue that might be predicted to alter the long-range tertiary structure of the protein.

TABLE 1

Characterization of Mutant p53 Proteins with Respect to The Site of Gene Mutation, Immunogenicity, and the Ability to Complex with HSP70 in 15 Breast Cancers

| Patient | Gene Mutation Sequence (Amino Acid) | (Codon exon) | Anti-p53 Antibodies | HSP Binding |
|---|---|---|---|---|
| 7 | TAT(Y) --> TGT(C) | 205 (6) | + | + |
| 11 | TAC(Y) --> TGC(C) | 163 (5) | + | + |
| 33 | TGT(C) --> GCT(R) | 275 (8) | + | + |
| 39 | CGC(R) --> CAC(H) | 175 (5) | + | + |
| 45 | TGT(C) --> CGT(R) | 238 (7) | + | + |
| 50 | Deletion | 174–181 (5) | + | + |
| 56 | CGC(R) --> CAC(H) | 175 (5) | + | + |
| 3 | CCT(P) --> GCT(A) | 278 (8) | − | − |
| 12 | CGT(R) --> TGT(C) | 273 (8) | − | − |
| 13 | CGG(R) --> CAG(Q) | 248 (7) | − | − |
| 17 | CGG(R) --> CTG(L) | 282 (8) | − | − |
| 24 | ATC(I) --> AAC(N) | 254 (7) | − | − |
| 43 | ATG(M) --> ATA(I) | 237 (7) | − | N.D. |
| 55 | TAC(Y) --> TGC(C) | 234 (7) | − | − |
| 63 | GGC(G) --> GAC(D) | 245 (7) | − | − |

Mutant proteins that induce an antibody response complex with HSP70.

Figures 3A, 3B:
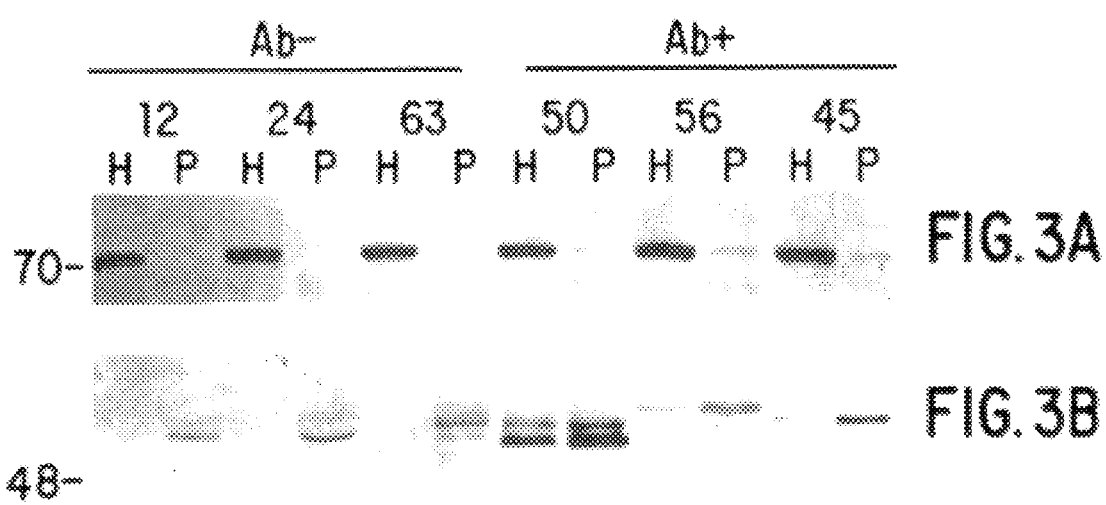
FIG. 3 shows the co-immunoprecipitation of p53 and HSP70 only in tumors from patients with anti-p53 antibodies. Protein extracts from tumor tissues were immunoprecipitated with an anti-p53 antibody (P) or anti-HSP70 antibody (H) and then probed with (A) rabbit anti-HSP70 sera and (B) PAb1801.

A similar clustering is evident in the human and murine mutant p53 proteins that have been analyzed for heat shock binding in tissue culture cells. p53 proteins containing mutations in exon 5 bind to a 70 kd heat shock protein while several proteins with mutations located in exon 8 fail to complex. See P. Hinds et al., Cell Growth Differ. 1, 571–580 (1990); O. Halevy et al., Science 250, 113–116 (1990). Given the possible function of an HSP70 in antigen presentation, it was of interest to determine whether the immunogenic p53 mutants formed complexes with this heat shock protein in vivo. Protein extracts from 14 of the 15 tumors containing p53 mutations were immunoprecipitated with anti-p53 and anti-heat shock antibodies. After blotting, separate membranes were probed with anti-p53 and heat shock antibodies in order to detect co-precipitation of these proteins. Tumor tissue from all seven patients with circulating p53 antibodies contained co-precipitating p53 and 70 kd heat shock proteins (FIG. 3). Conversely, no p53/heat shock protein complexes were detected in tissues from the seven patients lacking detectable p53 antibodies even though levels of both p53 and HSP70 comparable to the antibody-positive tissues were present. So, it does not appear to be an absence of either p53 or HSP70 that explains the lack of the complex. Since there are several species of 70 kd heat shock protein (i.e., hsp, hsc, and hsx) that are not distinguished using these antisera, it is possible that tissues which lack the complex do not synthesize the appropriate member of the heat shock protein family. However, different mutants have been shown, in rodent fibroblasts, to have different intrinsic abilities to complex with hsc70, see P. Hinds et al., supra; O. Halevy et al., supra, suggesting that a property intrinsic to p53 is responsible for complex formation in these breast cancers.

The findings in this study suggest a method for discriminating two classes of p53 mutations in human tumors. Several lines of evidence support the idea that this may be a functionally important way to categorize mutations. p53 mutations that bind heat shock protein are more potent dominant transforming genes in conjunction with ras. P. Hinds et al., *Cell Growth Differ.* 1, 571–580 (1990). It is possible that the heat shock protein/p53 complex facilitates p53-mediated transformation by sequestration of the wild-type tumor suppressor protein, perhaps more avidly than mutant p53 proteins that fail to complex with heat shock. There also appears to be a difference in the ability of mutant p53 proteins to function in transcriptional activation. A GAL4/p53 fusion protein containing a mutation at codon 273 (human) retains this function while a mutation at codon 135 (murine) destroys the ability to transactivate a GAL4 target sequence. L. Raycroft et al., *Science* 249, 1049–1051 (1990); S. Fields & S. Jang, *Science* 249, 1046–1049 (1990).

The difference between HSP-binding and -nonbinding p53 mutants in their ability to transform fibroblasts may, however, support the belief that inherited p53 mutations found in patients with Li-Fraumeni syndrome result in less potent oncogenes. These mutations appear to cluster around codon 250 of the p53 gene (S. Srivastava et al., *Nature* 348, 747 (1990); D. Malkin et al., *Science* 250, 1233 (1990)), and would therefore be predicted not to bind HSP and, perhaps, to be less oncogenic. Patient 63 from this study contained a mutation identical to one found in a Li-Fraumeni family (codon 245, Gly→Asp) and did not bind HSP in the breast cancer. This might explain why many of these patients can reach young adulthood before manifesting the characteristic malignancies of the syndrome despite having germ-line p53 mutations.

EXAMPLE 2

The following presents an immunoassay method for detecting the presence of p53 autoantibody in a patient's biological fluid, such as serum. This immunoassay method will be called the primary assay. Also presented is a modified version of the primary assay which functions as a confirmatory test and will be called the confirmatory assay. A sample which tested positive for p53 autoantibodies by the primary assay can be retested by the confirmatory assay to determine whether the sample is a true positive or a false positive. The general methods for conducting these assays, such as sandwich assays and competitive assays, are known to one skilled in the art. In the specific instance of this invention, the primary assay has two essential components: (1) solid phase bound p53 antigens (herein designated p53S), and (2) labelled antibodies directed to human immunoglobulins. The confirmatory assay includes the two components in the primary assay plus a third component: free (i.e. non-solid phase bound) competing p53 antigens (herein designated p53C).

Potential candidates for both p53S and p53C are wildtype or mutant full length native or recombinant p53 proteins and fragments thereof. Preferably, the fragments are natural, recombinant, or chemically synthesized polypeptides or peptides that are predominantly recognized by p53 autoantibodies. For example, these p53 proteins or fragments can be obtained from crude cell extracts or purified from naturally occurring or recombinant cells or cell lines. Examples of the sources for p53 proteins are cancer derived cell lines expressing different forms of mutant p53 proteins. For example, in the confirmatory assay described below under the section: "II. CONFIRMATORY ASSAY USING THE EIA FORMAT", inhibition of p53 autoantibody binding was observed with an extract of SW620 cells which provided p53C. Another source of p53C is the T-47D cell line (designated ATCC HTB 133, available from the American Type Culture Collection) which was derived from a breast tumor and expresses a mutant p53 protein in which a phenylalanine residue has been substituted for a leucine residue at codon 194. p53C has the additional requirement that it must not contain the crossreactive epitopes further described below with regard to p53S.

The solid phase which binds the p53S can be any of those used for immunoassays. They include natural and synthetic polymers, gels, and particles. The polymers can be cellulose or cellulose derivatives, fiberglass, and vinyl chloride. Labelled anti-human immunoglobulin antibodies are commercially available or can be made by one skilled in the art. The antibodies can be labelled with enzymatic, radioactive, fluorescent, or chemical labels.

In the primary assay, the patient's biological fluid is incubated over the solid phase, to which the p53S have been bound. The incubation period should be sufficiently long to allow the binding of the solid phase bound p53S to any anti-p53 autoantibody (herein designated ∂p53) that may be present in the patient sample to form a solid phase complex of {(p53S) (∂p53)}. Next, the unbound reagents are separated, e.g. the unbound reagents are dissolved in an aqueous medium and washed away from the solid phase, leaving behind the complex of {(p53S) (∂p53)} bound to the solid phase. Next, the solid phase is incubated with labelled anti-human immunoglobulin antibodies (herein designated *∂IgG) for a sufficient time to form the complex {(p53S) (∂p53) (*∂IgG)} which is bound to the solid phase, for patient samples containing p53 autoantibodies. This is followed by another separation step to remove the unbound reagents, leaving behind the solid phase bound {(p53S) (∂p53) (*∂IgG)} complex. The formation of the complex is detected by the label on the anti-human immunoglobulin antibodies. Thus, the formation of the {(p53S) (∂p53) (*∂IgG)} complex is directly proportional to the amount of p53 autoantibodies in the patient's serum.

It is to be noted that instead of having two incubation and wash steps (two-step assay), a single incubation and wash step (one-step assay) is also possible by simultaneously incubating the solid phase bound p53S, the *∂IgG and the patient's sample for a period sufficient for the formation of the solid phase bound {(p53S) (∂p53) (*∂IgG)} complex before washing off the unbound reagents and detecting the presence of the complex. Further, in both the one-step and two-step assays, one can also determine the amount of the remaining unbound *∂IgG, which would be inversely proportional to the presence of the p53 autoantibodies in a patient's sample.

If a patient's sample tests positive in the primary assay, it may be retested in the confirmatory assay. If the sample contains autoantibodies specific to p53 antigen, it will be identified as a true positive by the confirmatory assay. Likewise, if the sample contains antibodies which are not specific to p53 antigens but crossreact with p53S, it will be identified as a false positive by the confirmatory assay. The immunoglobulins in a patient's sample could crossreact with p53S for two reasons: 1) by its nature, the p53S used may contain crossreactive epitopes, e.g., a recombinant p53 protein may contain artificially introduced extraneous non-p53 structures (which facilitate the regulation, expression, or recovery of the p53 protein in cell culture productions) to which the patient's immunoglobulins bind; or 2) the binding of p53S to the solid phase may alter the structure of p53S such as to create crossreactive epitopes which are not natural to a p53 antigen.

The confirmatory assay is performed similarly to the primary assay except that the patient's sample is also incubated with the free competing p53 antigens (i.e. p53C). The patient's sample would be tested in two duplicate tests which are similar in all respects except that the first test contains p53C whereas the second test does not (the latter serves as the negative control). Thus, the second test can be the same as the primary assay except that in the confirmatory assay, this second test is run side-by-side with the first test. Alternatively, the second test can contain a control protein, cell extract, polypeptide, or peptide which does not cross-react with p53 autoantibodies. This protein, cell extract, polypeptide, or peptide will not be p53 protein or fragments thereof nor resemble p53 protein or fragments thereof such as would cross-react with p53 autoantibodies. Preferably, the form of the control, be it protein, cell extract, polypeptide, or peptide, is the same as the form used for p53C in the first test. That is, if the first test uses a p53 peptide fragment or a full length p53 as p53C, the second test will use a peptide fragment or a protein of equal length which is unrelated to p53. Similarly, if the first test uses a cell extract which contains p53 proteins as a source of p53C, the second test would use a cell extract which does not contain p53 proteins, as shown in the example below. In the first test, the patient's sample is premixed with p53C and then incubated with p53S. The p53C must not contain the crossreactive epitopes described above with regard to p53S. A source of p53C may therefore be a human cell line which produces high levels of native (be they wildtype or mutant) p53 antigens. One such cell line is SW620. During the incubation with p53S, the p53C would compete with the solid phase bound p53S for binding to the autoantibody specific for p53 antigens. The p53C would not compete with the solid phase bound p53S for binding to immunoglobulin crossreactive with p53S. It will be noted that the p53C should be used in an amount which would optimally inhibit the formation of the {(p53S) ($\partial$p53) (*$\partial$IgG)} complex. In the case of the confirmatory assay described herein, this amount could be determined, for example, by running the confirmatory first and second tests using patient samples which are known to contain p53 specific autoantibodies (the latter can be determined, for example, by immunoprecipitation described in Example 1) and comparing the results from the first and second tests. A 50 to 100% inhibition is preferred.

In the second test, the patient's sample is incubated with p53S in the absence of p53C. This test serves as the negative control. If the patient's sample contains autoantibody specific for the p53 antigen, the first test (which contains p53C) will have reduced formation of {(p53S) ($\partial$p53) (*$\partial$IgG)} complex as compared to its negative control counterpart and the sample will be identified as a true positive. If the patient's sample contains immunoglobulin crossreactive with p53S, the first test will not have reduced formation of the complex as compared to its negative control counterpart and the sample will be identified as a false positive.

Further, the confirmatory assay can be run alone, without the primary assay, to identify a patient's sample as a "true positive" for p53 autoantibody.

The above discussion and the following detailed description also show that if the solid phase bound p53S does not have epitopes which would cross-react with immunoglobulins that are not specific for p53 antigens, then the primary assay can be successfully used with this p53S without having to run a confirmatory assay.

Having described the primary and confirmatory assays in general, the following are specific examples of the assays as used in an enzyme immunoassay (EIA) format.

I. PRIMARY ASSAY FOR p53 AUTOANTIBODY USING THE EIA FORMAT (1) Immulon-4 microtiter plates (Dynatech Laboratories, Inc., Chantilly, Va.) were coated with 100 µl of coating solution per well at 37° C. for 2 hours. The coating solution contained 0.2 µg/ml recombinant human wild type p53 protein in 0.05M sodium bicarbonate/carbonate, pH 9.4. The recombinant p53 binds monoclonal antibodies PAb1801, PAb240, and PAb421 (Catalog Numbers Ab-2, Ab-3, and Ab-1, respectively, from Oncogene Sciences, Inc., Uniondale, N.Y). After the coating incubation, the wells were washed three times with wash buffer (0.05% Tween-20, 0.01% SDS, and 0.01% Thimerosal in phosphate buffered saline (PBS)). Then the wells were overcoated with 200 µl per well of 1% bovine serum albumin (BSA) in 0.01M sodium bicarbonate/carbonate, pH 9.4 for 1 hour at 37° C. After the overcoating step, the wells were washed as described above.

(2) To the wells were then added 100 µl of serum specimens which had been diluted 1000 fold in specimen diluent. These serum specimens were from patients with no clinical symptoms, patients with benign conditions, and patients with various cancers. The specimen diluent was at pH 6.8 and contained PBS and Tris as buffers; ethylene glycol-bis(β-aminoethyl ether)-N, N, N', N'-tetraacetic acid (EGTA) and ethylenediaminetetraacetic acid (EDTA) as metal chelators; Tween 20 as detergent to minimize nonspecific binding of human immunoglobulins; sodium azide as preservative; fetal calf serum and normal goat serum as protein stabilizers and to minimize nonspecific binding. Each diluted specimen was tested in replicate. Also, replicate wells were loaded with 100 µl of specimen diluent only which would yield "background" signal, 100 µl of a low positive control, and 100 µl of a high positive control. The positive controls were dedicated serum specimens positive for p53 autoantibody which had been diluted in specimen diluent to yield a "low" positive value and a "high" positive value, respectively, in the EIA. After all samples had been loaded in wells, the plate was covered and incubated overnight (16 to 18 hrs.) at room temperature.

(3) After the overnight incubation, the wells were washed four times with wash buffer. The wells were then loaded with 100 µl of conjugate solution. The conjugate solution was 0.2 µg/ml of goat anti-human IgG (H+L)-horseradish peroxidase conjugate (Catalog Number 04-10-06, Kirkegaard & Perry) in a conjugate diluent of pH 7.2. The conjugate diluent contained PBS and HEPES as buffers; benzyl alcohol as preservative; Triton x 100 as a detergent; fetal calf serum and normal goat serum as protein stabilizers and to minimize nonspecific binding.

The plates were incubated 2 hrs. at 37° C. After the conjugate incubation, the wells were washed four times as described above.

(4) After washing, the wells were loaded with 100 μl of OPD (ophenylenediamine-2HCl) substrate solution. The OPD substrate solution was prepared by dissolving one OPD tablet (In Vitro Test No. 7181E, Abbott Laboratories, Abbott Park, Ill.) per 5 mls. of diluent for OPD (In Vitro Test No. 5695, Abbott Laboratories, Abbott Park, Ill.). Plates were incubated in the dark at room temperature for 30 mins. after which 100 μl of 1N sulfuric acid were added per well. The absorbances of the wells were read at 492 nm using the Microplate Autoreader (#EL310, Bio-Tek Instruments, Burlington, Vt.).

(5) Averages of replicate absorbance values for each sample were calculated. The average "background" signal was subtracted from each sample average signal to correct for background absorbance. The corrected sample absorbances were divided by the corrected absorbance of the low positive control. These results yielded the p53 autoantibody values in units/ml of the serum specimens tested at a 1000-fold dilution. Serum specimens which, at a 1000-fold dilution, yielded an off-scale reading were further diluted to give on-scale readings, and the readings were readjusted to reflect the units/ml values for a 1000-fold dilution.

(6) A cutoff value of 0.427 units/ml was established for the primary assay which is the mean plus four standard deviations of 73 normal serum specimens. Serum specimens yielding values equal to or greater than 0.427 units/ml were scored positive for p53 autoantibody and the result of the assays is shown in Table 2 as follows:

TABLE 2

| SPECIMENS | TOTAL TESTED | # POSITIVE FOR P53* AUTOAB | % POSITIVE FOR P53* AUTOAB |
|---|---|---|---|
| NORMALS | 73 | 0 | 0 |
| BENIGN CONDITIONS | | | |
| Lung Benigns | 26 | 3 | 11.5 |
| Pneumonia | 20 | 0 | 0 |
| Lipemic | 12 | 1 | 8.3 |
| Rheumatoid Factor | 38 | 2 | 5.3 |
| **GI Benign | 26 | 2 | 7.7 |
| Ulcerative colitis | 20 | 0 | 0 |
| Cirrhosis | 12 | 0 | 0 |
| Diverticulitis | 10 | 0 | 0 |
| Pancreatitis | 10 | 0 | 0 |
| MALIGNANCIES | | | |
| Colon Cancer, CEA Negative | 84 | 13 | 15.5 |
| Colon Cancer, CEA Positive | 57 | 17 | 29.8 |
| Gastric Cancer | 29 | 4 | 13.8 |
| Lung Adenocarcinoma | 59 | 11 | 18.6 |
| Small Cell Lung Cancer | 52 | 12 | 23.1 |
| Breast Cancer | 66 | 7 | 10.6 |
| Ovarian Cancer | 43 | 8 | 18.6 |
| Head & Neck Cancer | 44 | 7 | 15.9 |
| Prostate Cancer | 46 | 7 | 15.2 |

*Autoab denotes autoantibodies
**GI denotes gastrointestinal.
Positive specimens ranged from 0.433 to 761 units/ml.

Figure 4:
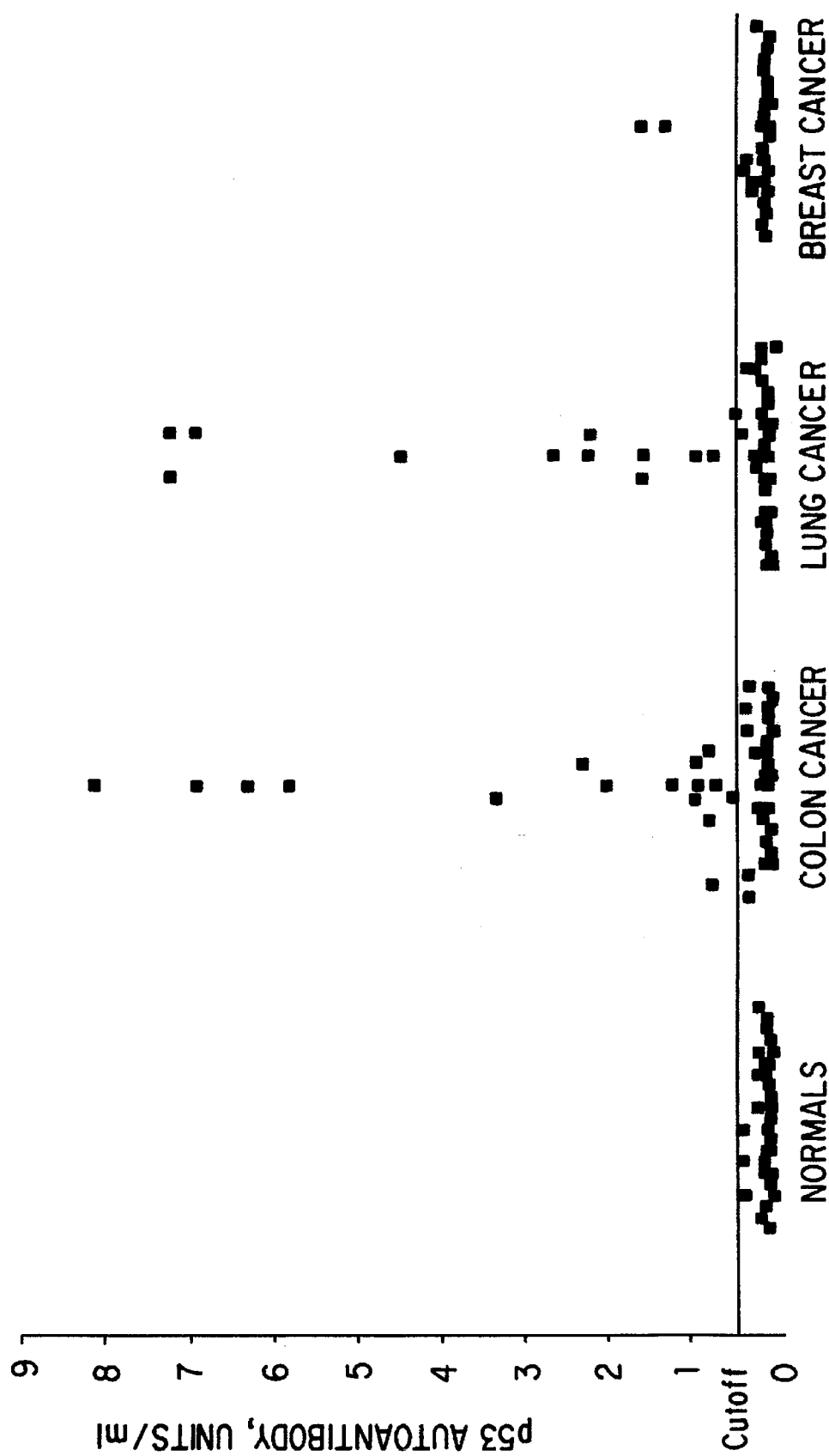
FIG. 4 shows the results of the primary assay in the enzyme immunoassay format to detect the presence of p53 autoantibodies in serum samples from normal people, and patients with colon Cancer, lung cancer, and breast cancer, respectively. The 0.427 units/ml cutoff value is also shown.

The cutoff values in future assays may be different, depending on the number of normal sera tested and the population from which such normal sera are drawn. Preferably, increased number of normal sera are used, and the sera are obtained from normal individuals who are representative of the patient population tested. FIG. 4 shows an example of p53 autoantibody values for a population of 34 normal individuals, 50 colon cancer, 43 lung cancer, and 32 breast cancer patients. In this specimen population, positive p53 autoantibody values ranged from just above the 0.427 units/ml cutoff value to 8.2 units/ml.

II. CONFIRMATORY ASSAY USING THE EIA FORMAT (1) Serum specimens which tested positive for p53 autoantibody in the primary assay described above were subjected to testing in the confirmatory assay. The confirmation assay procedure was essentially the same as that of the above EIA primary assay except for the preparation of the serum specimen (in step 2 of the above primary assay.). The serum specimen was diluted 1000 fold as described but added to it was a cancer cell line extract at a final concentration of 2 mg/ml extract protein. Each serum specimen, including the low and high positive controls, was tested this way in the presence of each of two different cell extracts. One cell extract was prepared from SW620 cells (Leibovitz, et al., Cancer Res. 36:4562–4569 (1976); the cell line has been deposited and designated ATCC CCL 227, available from American Type Culture Collection, Rockville, Md.).

This cell line was derived from lymph node metastasis of a primary colon cancer and expresses a mutant p53 protein in which a histidine residue has been substituted for an arginine residue at codon 273. The other extract was prepared from Saos-2 cells (designated ATCC HTB85, available from American Type Culture Collection, Rockville, Md.). This cell line was derived from osteosarcoma and it does not express any p53 protein because both p53 genes have been deleted.

(2) The above cell extracts were prepared as follows: Freshly grown cells were washed three times in cold PBS. Washed cells were suspended in cold lysis buffer at $50 \times 10^6$ cells/ml. (Lysis buffer is 50 mM Tris-HCl, pH 7.2, 5 mM EDTA, 150 mM NaCl, 0.5% Nonidet P-40 (NP-40, commercially available from Sigma Chemical Company, St. Louis, Mo.), 1 mM phenylmethylsulfonyl fluoride (PMSF), 1 µg/ml aprotinin, 1 µg/ml leupeptin, 5 mM NaF, and 1 mM $Na_3O_4V$.) The cellular suspension was sonicated for 15 sec. and then centrifuged at 100,000 X g for 1 hr. Supernatants were carefully removed and used as the cell extracts. Protein of the extracts were determined via the Bradford protein method (Catalog Number 500-0006, Bio-Rad Laboratories, Richmond, Calif.).

(3) The diluted serum specimen in the presence of cell extract was loaded in the wells and the EIA was taken to completion as described above for the primary assay (i.e. from steps 2 through 4 of the primary assay.). The principle of the confirmation EIA is that if the serum specimen contains autoantibody specific to p53, the SW620 extract will significantly decrease the EIA value compared to the Saos-2 extract. It is the mutant p53 protein in the SW620 extract which will specifically inhibit binding of the p53 autoantibody to the recombinant p53 protein coated on the wells. The Saos-2 extract will have no effect because it contains no p53 protein to compete for autoantibody binding to the recombinant p53 protein coated on the wells. If the serum specimen contains immunoglobulins which crossreact with the recombinant p53 protein coated on the wells, the SW620 extract will not significantly decrease the EIA value compared to the Saos-2 extract.

(4) After the confirmation EIA was run, the p53 autoantibody values in units/ml for each serum specimen tested in the presence of the SW620 and Saos-2 extracts were calculated as described above in step 5 of the primary assay. One modification was that all of the corrected sample absorbances were divided by the corrected absorbance of the low positive control tested in the presence of Saos-2 extract to yield units/ml p53 autoantibody. For each serum specimen the units/ml p53 autoantibody value in the presence of SW620 extract was subtracted from the units/ml p53 autoantibody value in the presence of Saos-2 extract. This difference was divided by the serum specimen's units/ml p53 autoantibody value in the presence of Saos-2 extract and multiplied by 100 to yield % inhibition. A serum specimen is scored a true positive for p53 autoantibody if 50 to 100% inhibition was observed. Table 3 summarizes the results of confirmatory assays of specimens which initially tested positive:

TABLE 3

| SPECIMENS | TOTAL TESTED IN CONFIRMATORY | # CONFIRMED TRUE POSITIVE | # CONFIRMED FALSE POSITIVE |
|---|---|---|---|
| BENIGN CONDITIONS | | | |
| Lung Benigns | 2 | 0 | 2 |
| Lipemic | 1 | 0 | 1 |
| Rheumatoid Factor | 1 | 0 | 1 |
| GI Bleed | 2 | 0 | 2 |
| MALIGNANCIES | | | |
| Colon Cancer | 27 | 25 | 2 |
| Gastric Cancer | 4 | 4 | 0 |
| Lung Adenocarcinoma | 13 | 12 | 1 |
| Small Cell Lung Cancer | 8 | 8 | 0 |
| Breast Cancer | 7 | 6 | 1 |
| Ovarian Cancer | 7 | 7 | 0 |

Some serum specimens when tested in the confirmatory assay showed 30 to 50% inhibition. This range of inhibition will require further study to determine if it is indicative of specific p53 autoantibody.

Figure 5:
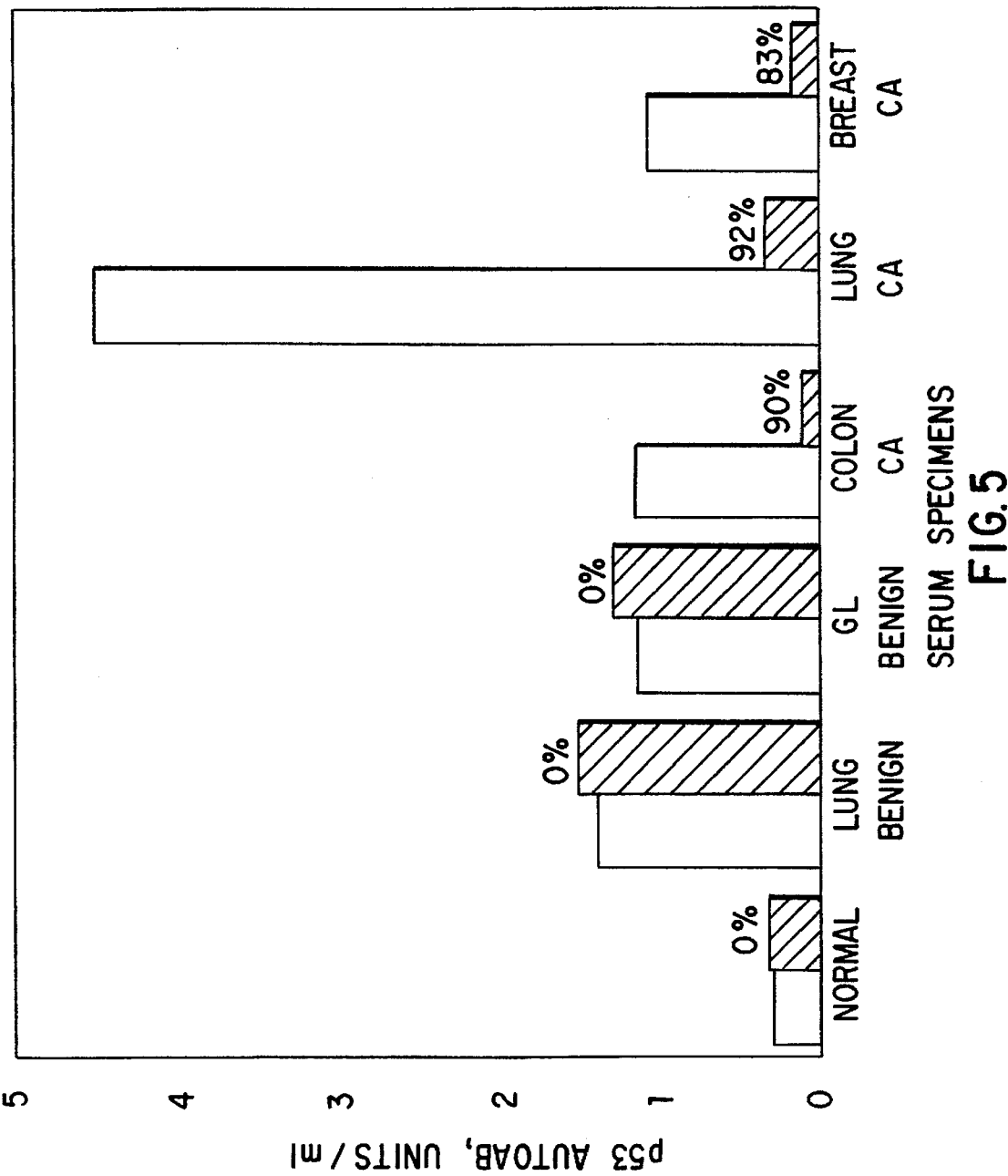
FIG. 5 shows the results of the confirmatory assay in the enzyme immunoassay format for confirming the presence of p53 autoantibodies from six serum specimens. "Ca" denosts cancer and "AUTOAB" denotes autoantibodies.

FIG. 5 shows the results of the confirmatory EIA for several individual specimens which, except for the normal specimen, had tested positive in the primary assay for p53 autoantibody. The two benign specimens shown, a lung benign and a GI benign, gave p53 autoantibody values of 1.32 and 1.136 units/ml respectively in the presence of Saos-2 extract. These values were not reduced in the presence of SW620 extract thus identifying them as false positives. In contrast the values of the three cancer specimens in the presence of SW620 extract were significantly reduced as indicated by the percentage reduction which prove that they were true positives.

The foregoing examples are illustrative of the present invention, and are not to be construed as limiting thereof. The invention is defined by the following claims, with equivalents of the claims to be included therein.

That which is claimed is:

1. A method of classifying tumor cells for the ability to elicit serum p53 autoantibodies in a patient carrying such tumor cells; comprising:

collecting a sample of tumor cells from said patient; and then detecting the presence of a complex in said tumor cells; said complex comprised of the p53 protein and a 70 kilodalton heat shock protein (hsp70);

the presence of said complex indicating said tumor cells are capable of eliciting serum p53 autoantibodies in said patient.

2. A method according to claim 1, wherein said detecting step is carried out by coimmunoprecipitation.

3. A method according to claim 1, wherein said detecting step is carried out concurrently with or after the step of removing said tumor from said subject.

4. A method according to claim 1, wherein said tumor cells are of epithelial origin.

5. A method according to claim 1, wherein said tumor cells are selected from the group consisting of colo-rectal, lung, breast, and ovarian cancer tumor cells.

* * * * *

UNITED STATES PATENT AND TRADEMARK OFFICE
CERTIFICATE OF CORRECTION

PATENT NO. : 5,652,115
DATED : July 29, 1997
INVENTOR(S) : Marks, et. al.

It is certified that error appears in the above-identified patent and that said Letters Patent is hereby corrected as shown below:

Title page, item [75], inventors: delete "Jerry G. Henslee, Libertyville, Ill.".

Column 3, line 18, change "colon Cancer" to --colon cancer--.

Column 7, line 3, change "PAb421" to --PAb 421--.

Signed and Sealed this

Sixteenth Day of December, 1997

Attest:

BRUCE LEHMAN

Attesting Officer

Commissioner of Patents and Trademarks